United States Patent [19]
Montevecchi et al.

[11] Patent Number: 5,728,069
[45] Date of Patent: Mar. 17, 1998

[54] DEVICE FOR THE PULSED PUMPING OF LIQUIDS, PARTICULARLY BLOOD

[75] Inventors: Franco Montevecchi, Felice-Segrate; Fabio Inzoli, Cesano Maderno; Stefano Rinaldi, Parma, all of Italy

[73] Assignee: Dideco S.p.A., Mirandola, Italy

[21] Appl. No.: 597,492

[22] Filed: Feb. 2, 1996

[30] Foreign Application Priority Data

Feb. 6, 1995 [IT] Italy ................... MI95A0203

[51] Int. Cl.⁶ .................................................. A61M 1/00
[52] U.S. Cl. .......................... 604/151; 604/131; 604/153; 600/16
[58] Field of Search ........................ 604/132, 141, 604/151, 153, 113; 600/16; 623/3; 417/562, 564, 566, 567, 569

[56] References Cited

U.S. PATENT DOCUMENTS

| | | | |
|---|---|---|---|
| 2,455,480 | 12/1948 | Hadley | 417/566 |
| 3,039,399 | 12/1962 | Everett | 604/153 |
| 3,148,624 | 9/1964 | Baldwin | 623/3 |
| 3,298,320 | 1/1967 | Latham | 604/153 |
| 3,955,557 | 5/1976 | Takagi | 600/16 |
| 4,084,606 | 4/1978 | Mittleman | 417/566 |
| 4,468,177 | 8/1984 | Strimling | 623/3 |
| 5,270,005 | 12/1993 | Raible | 604/4 |

*Primary Examiner*—Sam Rimell
*Assistant Examiner*—Luke Yeh
*Attorney, Agent, or Firm*—Popovich & Wiles, P.A.

[57] ABSTRACT

A device for the pulsed pumping of liquids, particularly blood, has a body in which are formed a pumping chamber in which a pulsed flow is imparted to the liquid, an inlet duct upstream of the pumping chamber and communicating therewith, and a delivery duct downstream of the pumping chamber and communicating therewith. Two valve members constituted by lip valves are provided for regulating the one-way flow of fluid in the body from the inlet duct to the pumping chamber and from the latter to the delivery duct. Low levels of hemolysis can be achieved, if the device is pumping blood. Moreover, the device has a low production cost and is quiet. The pumping device may be incorporated into a cardiopulmonary bypass device which includes a venous reservoir, a heat exchanger and an oxygenator.

59 Claims, 6 Drawing Sheets

18
DEVICE FOR THE PULSED PUMPING OF LIQUIDS, PARTICULARLY BLOOD

FIELD OF THE INVENTION

This invention relates to a device for the pulsed pumping of liquids, such as blood. More particularly, the invention is directed to a blood pump which may be incorporated into an integrated cardiopulmonary bypass system, the blood pump having a pumping chamber which receives blood through an inlet valve and discharges blood through a delivery valve and wherein at least one of the valves is a lip valve.

BACKGROUND OF THE INVENTION

Pumping devices are known in which a pumping chamber imparts a pulsed flow to a liquid. The device has two suitable directional valves, disposed upstream and downstream of the pumping chamber, respectively, which regulate the inlet flow into the chamber and the output flow therefrom. One application for such a device is as a blood pump. Such a blood pump may be used, for example, to replace the heart function in clinical or surgical cases such as heart bypass surgery.

Various kinds of directional valves are used in these devices. For example, valves with movable members which are moved by the fluid, such as mechanical ball valves or disc valves, and biomorphous valves, are used. However, the performance of these valves in blood pumps has not been satisfactory. These valves are generally positioned in a duct section having a cylindrical or similar shape which is intended to admit the fluid to the pumping chamber or to discharge it therefrom. Sometimes, they are derived from valves developed and used for prosthetic implants. In such cases they may be characterized by some structural simplifications and/or by materials with a shorter expected working life and/or by different shapes of the regions for connection to the pumping chamber. These features make it difficult to adapt these valves for use in pulsatile blood pumps. This type of valve has the additional disadvantage of having restricted areas for the passage of blood. These restricted flow areas increase the chances of causing blood damage and hemolysis. This makes it difficult for pumps with these valves to achieve the low level of hemolysis and blood damage levels which are desirable for blood pumps. Moreover, these restricted areas are located in positions which do not permit optimization of the fluid dynamics of pulsed pumping devices when they are integrated with other components such as oxygenators, heat exchangers, filters, venous reservoirs, etc. These valves are also subject to certain additional problems. For example, mechanical valves have the additional disadvantage of noise. Biomorphous valves are subject to significant deformation during operation and, therefore, experience considerable stresses. Further, given their geometrical complexity, they have high production and quality control costs.

Another group of valves are characterized by controlled obstruction devices. These devices obstruct the inlet duct and the delivery duct connected to the pumping chamber. These devices may also take the form of obstructers of deformable pipes which bring about closure by squeezing the pipes. These devices also have the disadvantage of causing hemolysis resulting from the operation to obstruct the pipes.

The valve function may also be performed by cutting-off the inlet and delivery areas by particular geometry and movements of movable walls of the pumping chamber. These movable walls may perform this function either by deformation of the wall of the pumping chamber or by the presence of elements which may be rigid, and which are capable of rotary-translatory motion inside the pumping chamber. In this case also, the cutting-off involves a fluid dynamic design which is not optimized from the point of view of minimizing hemolysis. Moreover, the system is complex and therefore involves high production costs.

SUMMARY OF THE INVENTION

The object of the present invention is to present a pulsed pumping device which can avoid the aforementioned disadvantages of the prior art.

This object is achieved by means of a device for the pulsed pumping of liquids, particularly blood. The device comprises a body in which is formed a pumping chamber in which a pulsed flow is imparted to the liquid, an inlet duct upstream of the pumping chamber and communicating therewith, and a delivery duct downstream of the pumping chamber and communicating therewith. The device also comprises a first valve member which cuts off the inlet flow of the liquid into the pumping chamber and a second valve member which cuts off the output flow of the liquid form the pumping chamber. At least one of the first and second valve members is a lip valve, one side of which is fixed in the body and which can bend between a position in which communication between the duct and the pumping chamber is closed and a position in which the communication is open, depending on the fluid dynamic forces acting on the lip valve. A diaphragm within the pumping chamber is driven by an actuator in a reciprocating manner to impart fluid dynamic forces which open and close the valves. The lip valves and the diaphragm may have various alternative configurations. The pump may be incorporated into a cardiopulmonary bypass device which may include a venous reservoir, an oxygenator and a heat exchanger.

BRIEF DESCRIPTION OF THE DRAWINGS

For a better understanding of the invention, a description is given below of embodiments thereof illustrated in the appended drawings, in which.

DETAILED DESCRIPTION OF THE INVENTION

The Pulsed Pumping Device

Figure 1:
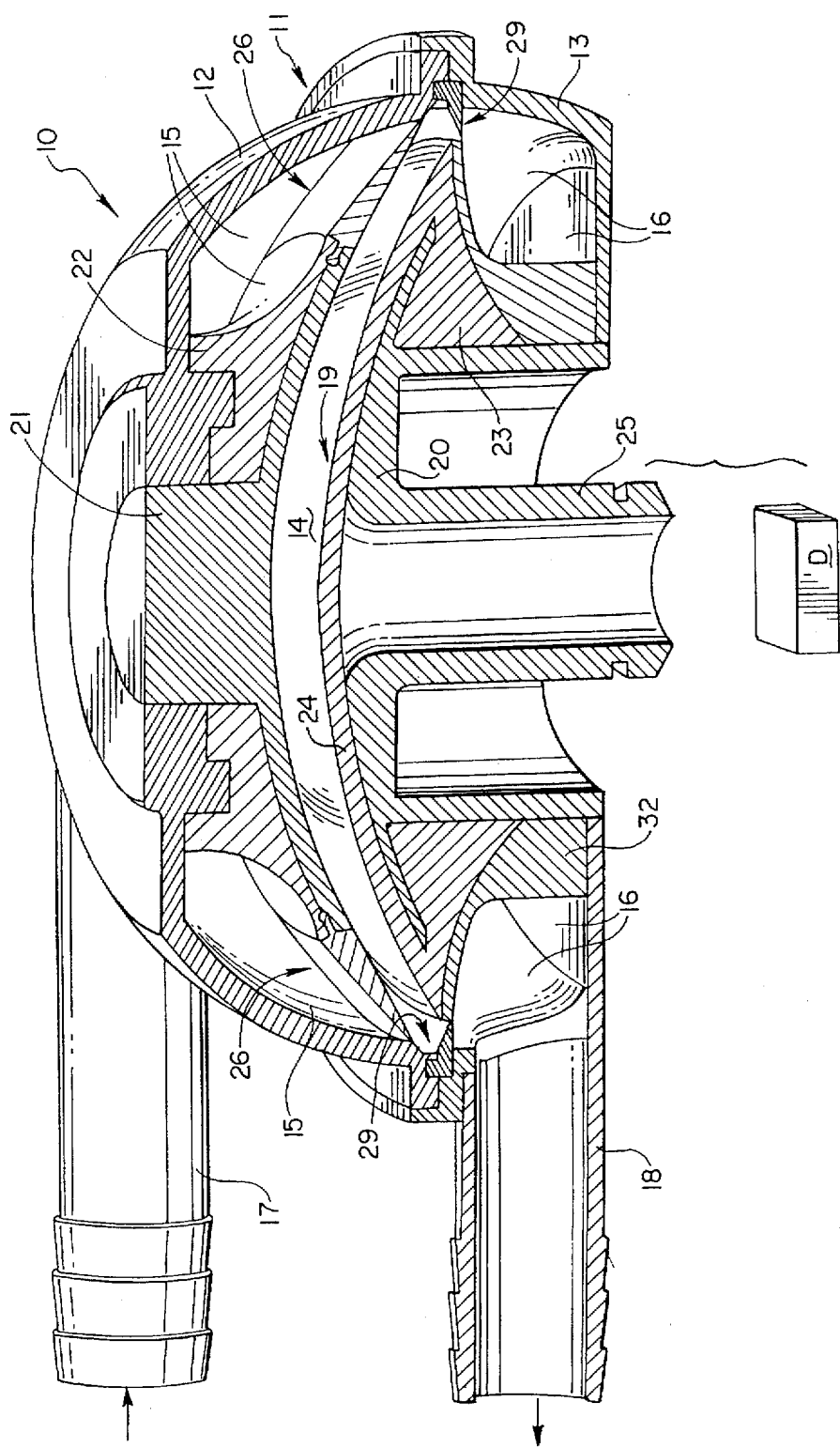
FIG. 1 is a perspective view, in section, of a pumping device according to the invention.
Figure 2:
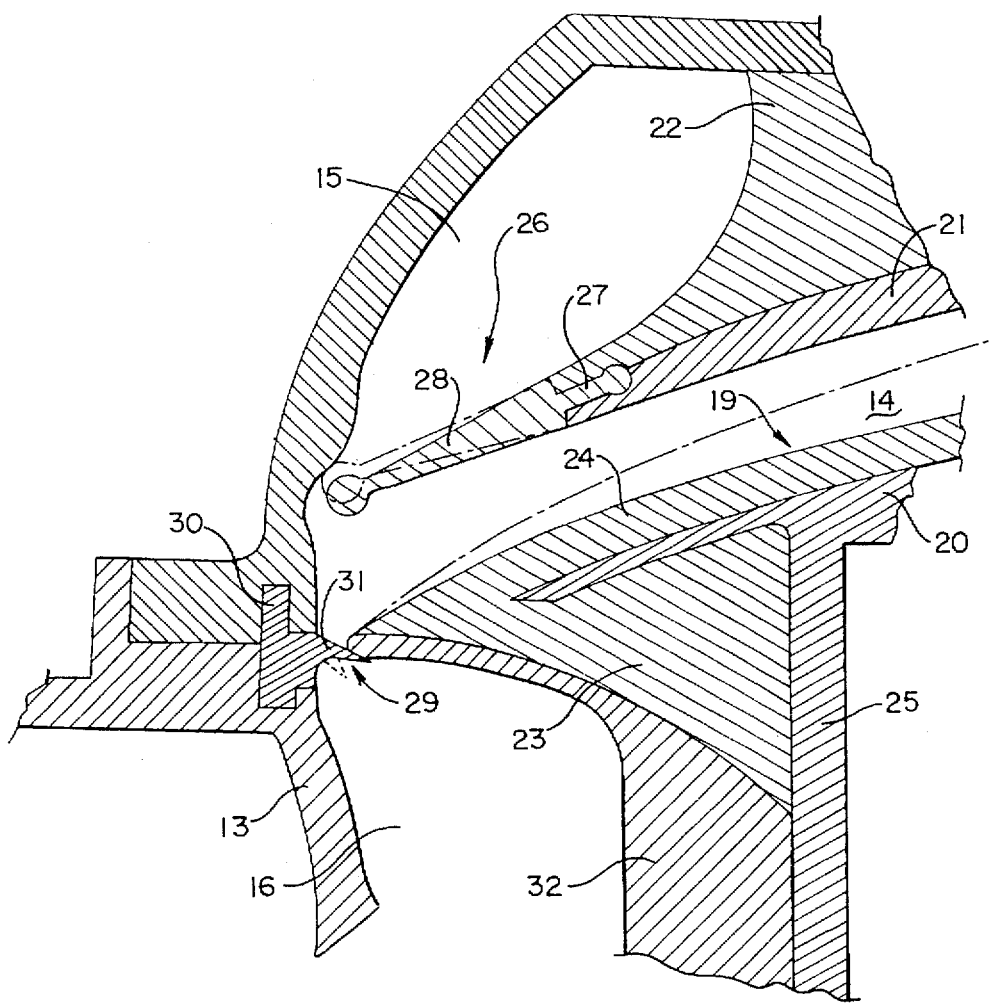
FIG. 2 is a radial section of a detail of the device of FIG. 1, showing the operation of pumping and valve elements of the device of FIG. 1, FIGS. 3 and 4 show variants of the valve elements of the device of FIG. 1 and FIGS. 5 and 6 are perspective views, in section, of two further pumping devices according to the invention, each incorporating a venous reservoir, a heat exchanger and an oxygenator.

The pumping device shown in FIGS. 1 and 2 and generally indicated 10, has a circular body 11 comprising an upper half shell 12 and a lower half shell 13 fixed to one another. Inside the body 11 there is a circular pulsed pumping chamber 14, an annular inlet duct 15 formed in the half shell 12 upstream of the chamber 14 and communicating therewith, and an annular delivery duct 16 formed in the half shell 13 downstream of the chamber 14 and communicating therewith. There are also an external inlet connector pipe 17 and an external output connector pipe 18 formed integrally with the half shell 12 and with the half shell 13, respectively.

The bottom of the chamber 14 is defined by a circular, resilient diaphragm 19 mounted on a lower support 20 fixed to the half shell 13. The top of the chamber 14 is defined by a dome 21, opposite the diaphragm 19 and fixed to the half shell 12 and to an upper support 22 which in turn is fixed to the half shell 12 and defines the duct 15. The diaphragm 19 comprises an annular portion 23 which fixes the diaphragm 19 to the support 20 and an expansible convex portion 24. The support 20 comprises a supply connector pipe 25 for connection to an actuating fluid supply line of a fluid dynamic actuating device of known type shown schematically by a block D.

Between the annular inlet duct 15 and the pumping chamber 14 there is a resilient, annular inlet lip valve 26 comprising an anchoring portion 27 and a projecting portion 28. The anchoring portion 27 is housed in a corresponding seat formed partly in the dome 21 and partly in the support 22 so as to anchor the valve 26 to these latter elements. The projecting portion 28 decreases gradually in cross section towards its free end but has a thickened portion at the very end.

Between the pumping chamber 14 and the annular delivery duct 16 there is another resilient, annular delivery lip valve, indicated 29. The valve 29 comprises an anchoring portion 30 and a projecting portion 31. The anchoring portion 30 is housed in a corresponding seat formed partly in the half shell 12 and partly in the half shell 13 so as to anchor the valve 29 to these latter elements. The cross section of the projecting portion 31 decreases gradually towards its free end.

The body 11 of the device may be made of polycarbonate, whereas the lip valve 26 and 29 may be made of polyurethane. The device 10 described and illustrated is intended for pumping liquids in general and is intended particularly for pumping blood.

Operation of the Pulsed Pump

During operation, the pipe 17 is suitably connected to a blood inflow line and the pipe 18 to a blood outflow line. The device D acts on the diaphragm 19 with alternating pressure by means of the actuating fluid which flows through the pipe 25. In particular, the actuating fluid acts on the opposite face of the diaphragm to the face which faces the chamber 14. The diaphragm is thus moved in a reciprocating manner as indicated by the broken line in FIG. 2, returning to the initial position shown in continuous outline. A pressure and a vacuum are correspondingly created alternately in the pumping chamber 14.

When a vacuum is created in the chamber 14, the projecting portion 28 of the valve 26 is in the position in which it is moved away from the adjacent wall of the half shell 12 and thus allows blood to be drawn into the chamber 14 from the inflow line through the pipe 17 and the duct 15. At the same time, the projecting portion 31 of the valve 29 presses against the facing wall of an element 32 defining the duct 16 and thus prevents the blood from flowing from the chamber 14 into the duct 16. Conversely, when pressure is created in the chamber 14, the projecting portion 28 of the valve 26 is moved and presses against the wall of the half shell 12 as indicated in broken outline in FIG. 2 and thus prevents the blood from returning to the duct 15 from the chamber 14. At the same time, the projecting portion 31 of the valve 29 is moved away from the wall of the element 32, as indicated in broken outline in FIG. 2, thus allowing blood to be sent to the outflow line through the duct 16 and the pipe 18. The device 10 thus performs its pulsed pumping function and the lip valves 26 and 29 enforce a one-way flow of blood inside the device.

Further Lip Valve Embodiments

Figure 3:
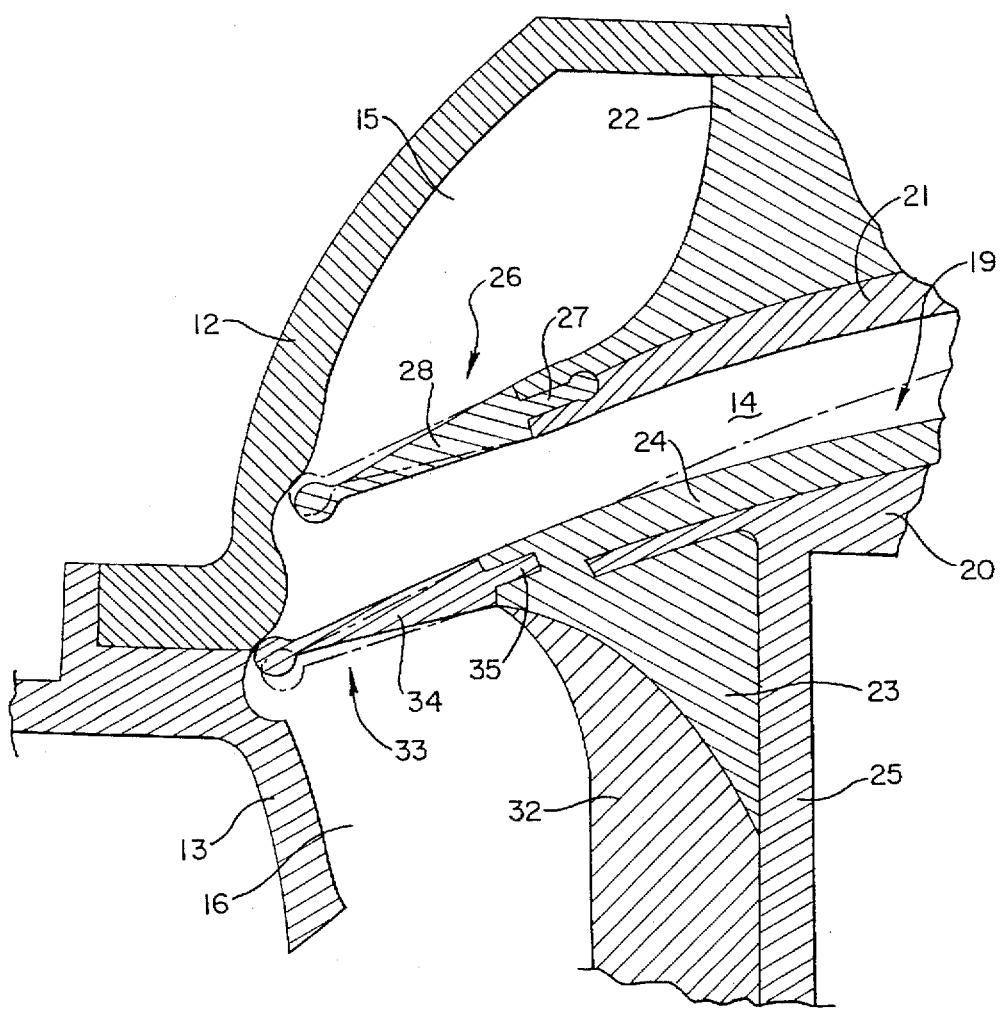

FIG. 3 shows a variant of the delivery lip valve. In this case, the delivery valve, indicated 33, has essentially the same configuration as, and is disposed on the same side as, the inlet valve 26. In particular, the valve 33 has a projecting portion 34 identical to the projecting portion 28 of the valve 26 and an anchoring portion 35 of a different shape, housed in a corresponding seat formed in the diaphragm 19. The projecting portion 34 of the valve 33 interacts with the wall of the half shell 12. Naturally, there are changes in the configurations of some components in comparison with the previous embodiment to allow for this different configuration of the delivery valve. The operation of the valve 33 is the same as that described above for the valve 29.

Figure 4:
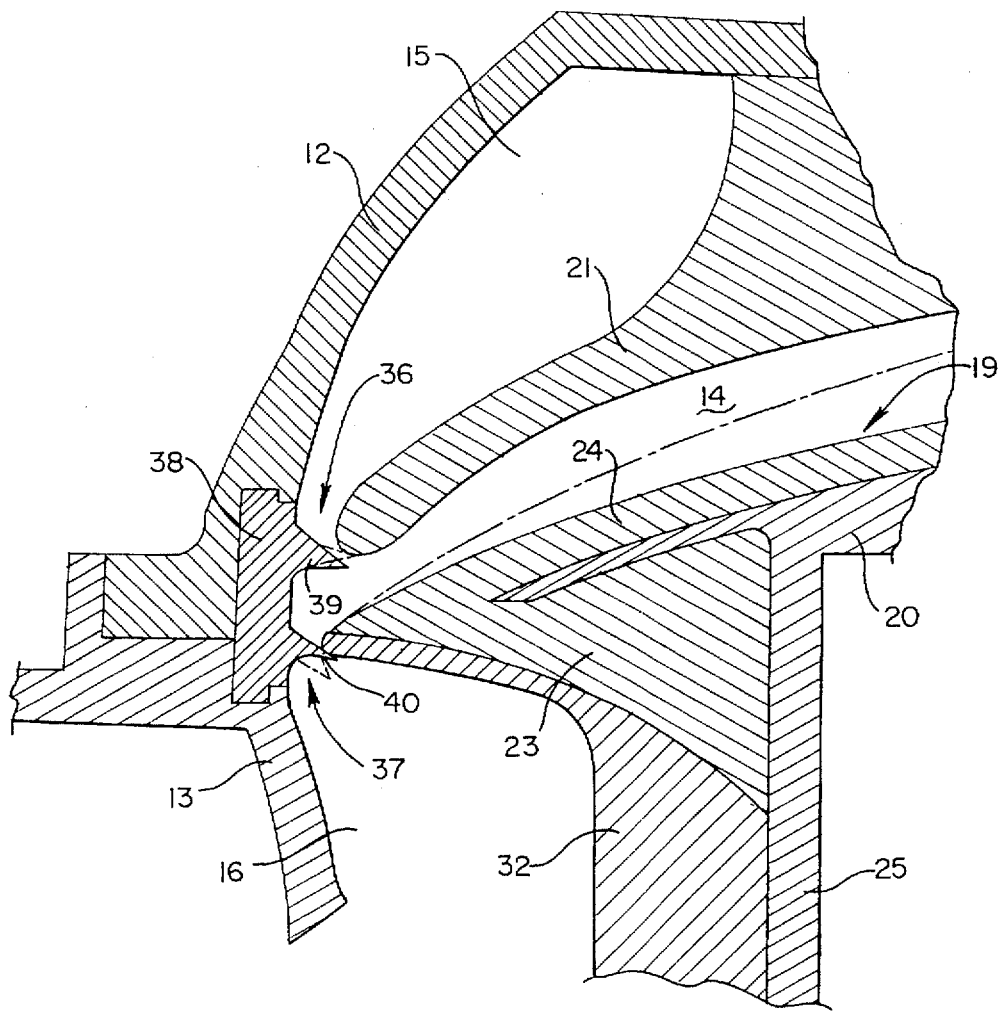

FIG. 4 shows another variant relating to the valves. In particular, it has an inlet lip valve 36 and a delivery lip valve 37 which are formed by a single element. The valves 36 and 37 have a common anchoring portion 38 and each has a respective projecting portion, indicated 39 for the valve 36 and 40 for the valve 37. The common anchoring portion 38 is housed in a corresponding seat formed partly in the half shell 12 and partly in the half shell 13. The projecting portions 39 and 40 are disposed on the same side as, and have the same shape as, the projecting portion 31 of the delivery valve 29 of the first embodiment. The projecting portion 39 of the valve 36 interacts with the facing wall of the dome 21. Naturally, there are changes in the configurations of some components in comparison with the first embodiment to allow for this different valve configuration. The operation of the valves 36 and 37 corresponds to that of the preceding valves.

The pulsed pumping device described above has many advantages. The lip valves permit large inflow and outflow areas for the biological liquid and therefore reduce pressure losses and bring about conditions of very limited fluid dynamic stresses with a consequent reduction of the levels of blood damage. Moreover, although the opening movements of the valves provide large flow areas, they are of small magnitude and the inertia involved is thus also very small. Opening is consequently immediate and in time with the pumping action, and pressure losses and turbulence are reduced. Further, by virtue of this minimal opening movement, the deformations of the valve structures, and hence the stresses thereon, are extremely limited.

Given its particularly simple shape, the lip valve is suitable for production by low cost techniques. The simplicity of shape also results in ease of assembly and in a simplification of the necessary quality control.

Integrated Cardiopulmonary Bypass Device

Although pulsed pumping devices with lip valves may be used as separate components as discussed above, their construction is particularly well suited for adaptation in an integrated cardiopulmonary bypass device. The specific annular configuration of the lip valves involves considerable simplifications for the integrated production, in axially symmetrical form, of sets of inlet and delivery valves in an integrated structure, or of integrated sets of valves and pumping chamber walls. In particular, this annular configuration is advantageous when the pumping device is associated with devices involved in the processing of biological liquids (i.e. blood), such as heat exchangers, oxygenators, filters, venous reservoirs or the like. In fact, since coupling does not have to take place in regions of reduced blood flow as with conventional valves which require small circular areas, it is possible to produce a compact, inexpensive integrated device with limited dimensions. Moreover, by using lip valves optimal fluid dynamic conditions are achieved and dead spaces are reduced.

Figure 5:
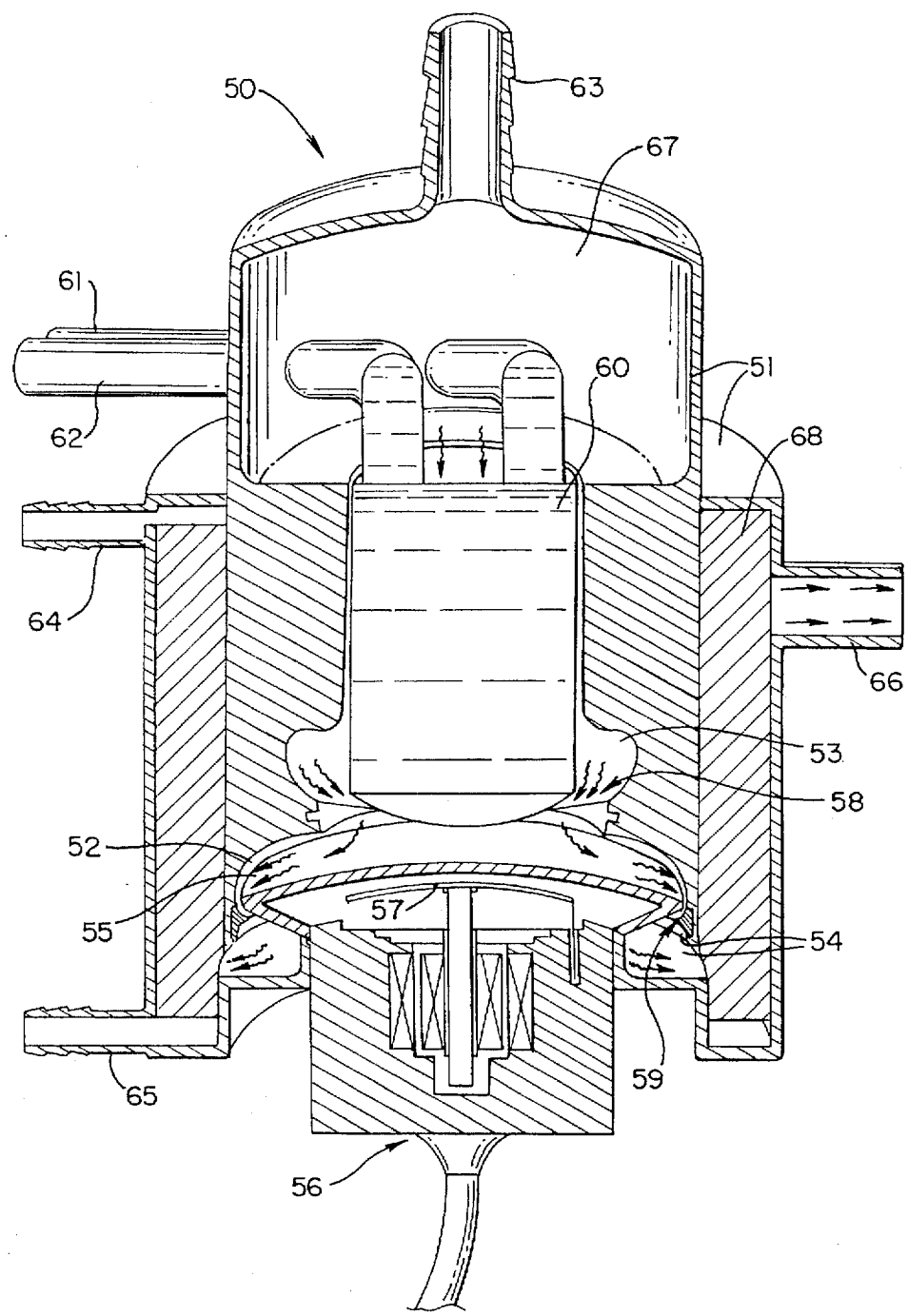
Figure 6:
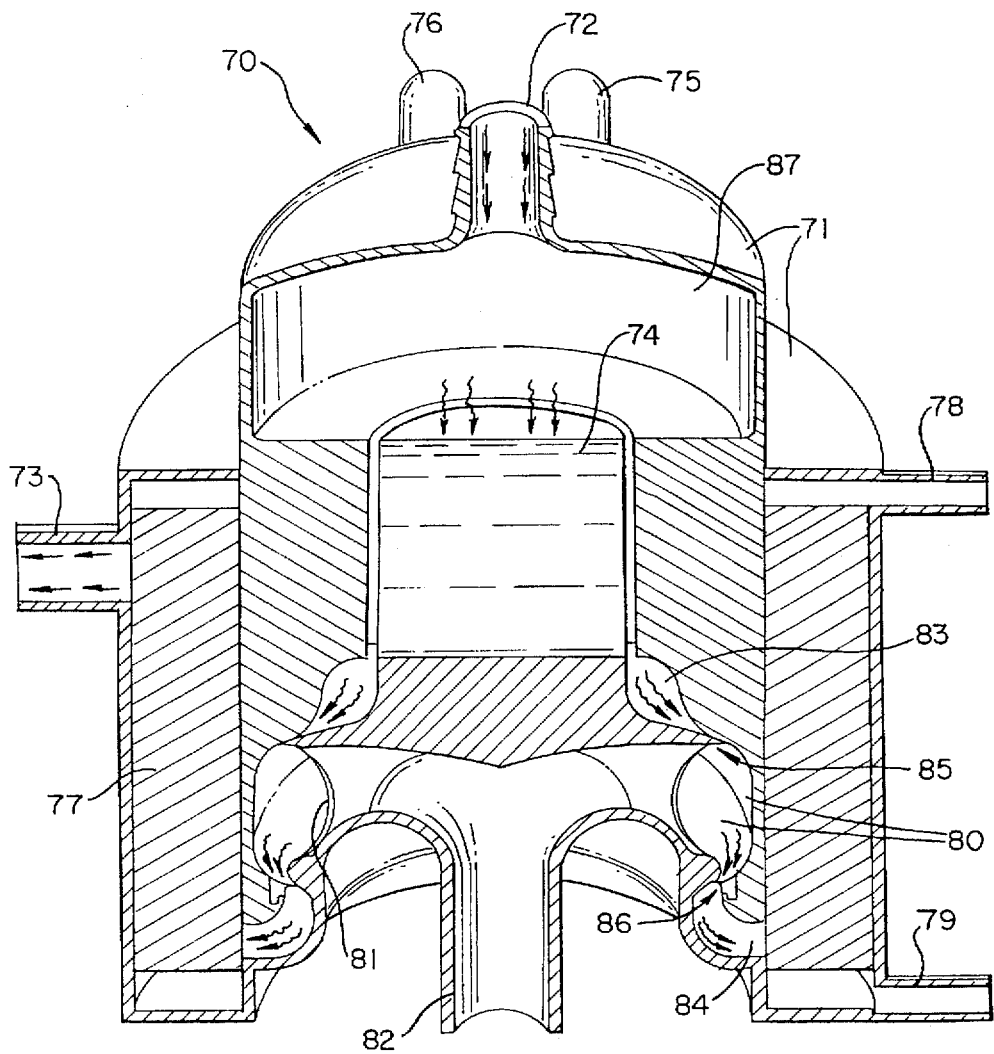

FIGS. 5 and 6 show two blood pumping devices with pumping diaphragms and annular lip valves, each device incorporating a venous reservoir, a heat exchanger and an oxygenator. The device of FIG. 5, generally indicated 50, comprises a substantially cylindrical body 51 in the bottom of which are a circular pulsed pumping chamber 52, an annular inlet duct 53 and an annular delivery duct 54. A diaphragm 55, which defines the bottom of the chamber 52, is operated by an electromechanical actuator 56 of known type comprising a plate 57 acting on the diaphragm 55 with a reciprocating motion. The annular inlet lip valve, indicated 58, has a configuration corresponding to that of the valves 26 and 33 of FIGS. 1, 2 and 3, but has the projecting portion facing inwardly. The annular delivery lip valve, indicated 59, has a configuration corresponding to the valve 29 of FIGS. 1 and 2.

Upstream of the inlet duct 53, the body 51 contains a substantially cylindrical heat exchanger 60, for example, of the known type with plates, which is coaxial with the circular chamber 52 and with the annular ducts 53 and 54. A route along which a heat exchanger fluid, for example, water is circulated, and a route for the blood which is in thermal contact with the fluid through suitable exchange walls, are defined in the heat exchanger. The route for the exchange fluid is connected to the exterior by means of exchange fluid inlet and outlet pipes 61 and 62. The route for the blood is connected, on one side, to a substantially cylindrical venous reservoir 67 formed in the body 51 and communicating with the exterior in turn by means of an axial blood inlet pipe 63. On the other side, the route for the blood is connected to the annular inlet duct 53.

Downstream of the delivery duct 54 the body 51 contains an oxygenator 68, for example, of the known type with a hollow fiber bundle comprising layers of microporous hollow fiber membranes having an annular configuration, coaxial with and outside the heat exchanger 60. A route along which the oxygen is circulated and a route for the blood enabling the exchange of gases through suitable exchange walls are defined in the oxygenator 68. The route for the oxygen is connected to the exterior by means of an oxygen inlet pipe 64 and an oxygen outlet pipe 65. The route for the blood is connected to the annular delivery duct 54 on one side and to a blood outlet pipe 66 on the other side.

During operation of the device pipes 61 and 62 are connected to exchange fluid supply and intake lines, respectively. The pipes 64 and 65 are connected to oxygen supply and intake lines, respectively. The pipes 63 and 66 are connected to blood inflow and outflow lines, respectively. The route of the blood through the device 50 is indicated by arrows. In particular, the reciprocating movement of the diaphragm 55 draws the blood into the device from the supply line into the venous reservoir. The blood then flows into the heat exchanger 60 in which it is heated or cooled by the heat exchanger liquid. From the heat exchanger 60, the blood reaches the duct 53 and, from there, reaches the pumping chamber 52 through the valve 58 and then the delivery duct 54 through the valve 59. The blood then passes through the oxygenator 68, in which it receives oxygen, and is discharged form the device 50 through the blood outlet pipe 66.

Thus, a pulsed pumping device with one or more lip valves of varying configurations may be advantageously combined in an integrated device which, in addition to the pumping function, also performs the venous reserve, heat exchange and oxygenation functions. The device is compact and inexpensive. Moreover, as mentioned above, the various generally circular/cylindrical shapes of the elements which make up the device achieve optimal fluid dynamic conditions as well as reducing the dead spaces.

A further embodiment of such an integrated device is shown in FIG. 6. The device of FIG. 6, generally indicated 70, has many similarities with the device of FIG. 5. It also has a substantially cylindrical body 71, a blood inlet pipe 72 and a blood outlet pipe 73, a substantially cylindrical venous reservoir 87, a substantially cylindrical heat exchanger 74, for example, of the plate type, connected to exchange fluid inlet and outlet pipes 75 and 76, and an annular oxygenator 77, for example of the hollow fiber microporous membrane type, connected to oxygen inlet and outlet pipes 78 and 79. However, unlike the device of FIG. 5, the shape of the pulsed pumping chamber 80 is annular, and the shape of the diaphragm, indicated 81, is also annular with a substantially "C" shaped cross section. The diaphragm has a concaved outer face, its concavity facing the chamber 80 and defining the chamber on one side. The diaphragm 81, which is of the fluid dynamic type, operates in a manner similar to that of the device of FIG. 1, by means of an inlet pipe 82 connected to a fluid dynamic actuating device. The inlet and delivery ducts, indicated 83 and 84, also have different shapes from those of the device 50 of FIG. 5. The inlet and delivery valves, indicated 85 and 86, respectively, correspond to those of the device 10 of FIG. 1. The operation of the device 70 is similar to that of the device 50 and the route followed by the blood is again indicated by arrows. In this case, however the diaphragm 82 moves radially. The advantages of the device 70 are the same as those of the device 50.

From the foregoing detailed description of specific embodiments of the invention, it should be apparent that an improved device for the pulsed pumping of liquids, particularly blood, has been disclosed. Although particular embodiments of the invention have been disclosed herein in detail, this has been done for the purpose of illustration only, and is not intended to be limiting with respect to the scope of the appended claims, which follow.

For example, with reference to the lip valves, the shape and/or the thickness of the anchoring portion may vary in dependence on the operating parameters required (area of passage, gradient of the pressure applied, etc.). As seen in the embodiments shown by way of example, the projecting portion may be designed so as to decrease to a minimal thickness or may be enlarged at the movable end. They may have any other geometrical shape suitable for satisfying particular methods of contact and for withstanding stresses in the valve structure or for achieving different fluid dynamics. The inlet and delivery lip valves may be disposed on the same side or on opposite sides. Both may be directed inwardly or outwardly or one may be directed outwardly and the other inwardly. Moreover, they may both be directed downwardly or upwardly or one may be directed downwardly and the other upwardly, or in any intermediate direction.

The annular mobility of the lip valves has been found particularly advantageous, as described above. However, the valves may be designed with mobility of only a limited sector of the valve. In this case, the required area for the passage of the fluid through the valve may involve an increase in the aperture of the valve, this aperture in any case remaining limited and compatible with low levels of stressing of the material.

A lip valve having a configuration other than the annular configuration could also be considered. It may be continuous or discontinuous, for example, with a segmented annular configuration. The annular configuration is not necessarily circular but may also be elliptical, etc.

The pumping chamber and the resilient diaphragm may also have different shapes and, as seen in the embodiments described by way of example, the diaphragm may be operated by a fluid dynamic or electromechanical device.

The use of other types of pulsed pumping devices, for example, comparable to centrifugal pumps may be considered. Further, only one of the two inlet and delivery valves in the pumping device may be in the form of a lip valve, the other valve remaining conventional. In the case of the pumping of blood, the inlet and/or delivery duct may be resiliently collapsible so as to form atrial and/or ventricular sacs.

Pumping systems similar to that described may be arranged in series. For example, a first pumping system may be intended for drawing in the biological liquid and may be controlled in a manner such as to optimize and rapidly fill the actual pumping chamber of a second, downstream pumping system. In the case of the pumping of blood, the first pumping system thus forms an active valve controlled atrium.

Additionally it is possible to provide for variants of the shape of the body of the device and of its components. This applies both to the simple device, that is the pump alone, and to the integrated multi-function device. The integrated multi-function device may incorporate one or more devices for processing the blood which may be those described or others, for example, filters.

Although the embodiment's of the integrated cardiopulmonary device shown in FIGS. 5 and 6 have the heat exchanger and oxygenator located upstream and downstream of the pump, respectively, this should not be construed as limiting the scope of the present invention. Specifically, any of the components of the device including the heat exchanger and oxygenator may be either upstream or downstream of the pump along the blood flow route.

Further, the device described above may be used for the pulsed pumping of liquids other than blood or other biological fluids.

We claim:

1. A device for the pulsed pumping of liquids, particularly blood, comprising;

a body portion;

a pumping chamber disposed within the body portion;

an inlet duct in fluid communication with the pumping chamber;

a delivery duct in fluid communication with the pumping chamber;

an inlet valve for controlling the flow of liquid from the inlet duct into the pumping chamber; and a delivery valve for controlling the flow of liquid from the pumping chamber to the delivery duct, at least one of the inlet valve and delivery valve being an annular lip valve for sealing an annular opening, the valve being located within the body portion and being movable between an open position and a closed position in dependence of fluid dynamic forces acting on the at least one lip valve.

2. The device of claim 1 wherein both the inlet valve and the delivery valve are lip valves.

3. The device of claim 1 wherein one side of the at least one lip valve is fixed in the body portion.

4. The device of claim 1 further including a diaphragm disposed within the pumping chamber, the diaphragm being movable between a first position and a second position in a reciprocating manner such that pulsed flow is imparted to the liquid.

5. The device of claim 1 further including a fluid dynamic actuating device to impart fluid dynamic force to the liquid in the pumping chamber.

6. The device of claim 5 further including a diaphragm which is driven in a reciprocating manner by the actuating device between a first position and a second position such that pulsed flow is imparted to the liquid.

7. The device of claim 4 wherein the diaphragm has a circular configuration.

8. The device of claim 6 wherein the diaphragm has a circular configuration.

9. The device of claim 4 wherein the diaphragm has an annular configuration and a substantially "C" shaped cross section.

10. The device of claim 6 wherein the diaphragm has an annular configuration and a substantially "C" shaped cross section.

11. The device of claim 7 wherein the pumping chamber, the diaphragm, the inlet duct, the delivery duct, and the at least one lip valve are coaxial.

12. The device of claim 9 wherein the pumping chamber, the diaphragm, the inlet duct, the delivery duct, and the at least one lip valve are coaxial.

13. The device of claim 1 wherein the at least one lip valve comprises a first portion for anchoring the lip valve to the body portion and a second projecting portion which moves between the open position and the closed position.

14. The device of claim 2 wherein the lip valves comprise a first portion for anchoring the lip valve to the body portion and a second projecting portion which moves between the open position and the closed position.

15. The device of claim 1 further comprising a blood processing device selected from a venous reservoir, heat exchanger, and an oxygenator, the blood processing device being disposed on a route along which the blood flows inside the body of the pumping device.

16. The device of claim 15 wherein the blood processing device, the pumping chamber, the diaphragm, the inlet duct, the delivery duct and the at least one lip valve are coaxial.

17. A cardiopulmonary bypass device comprising:

a body portion having a blood inlet and a blood outlet and between which is disposed a blood flow route;

a pump disposed within the body portion for the pulsed pumping of blood along the blood flow route, the pump including a pumping chamber, an inlet duct in fluid communication with the pumping chamber, a delivery duct in fluid communication with the pumping chamber, an inlet valve for controlling the flow of blood from the inlet duct into the pumping chamber, a delivery valve for controlling the flow of blood from the pumping chamber to the delivery duct, at least one of the inlet valve and the delivery valve being an annular lip valve for sealing an annular opening, the valve being located within the body portion and having a projecting portion movable between an open position and a closed position in dependence of fluid dynamic forces acting on the at least one lip valve; and an oxygenator disposed within the body portion, the oxygenator having an inlet and an outlet through which blood flows along the blood flow route.

18. The device of claim 17 further including a diaphragm disposed within the pumping chamber, the diaphragm being movable between a first position and a second position in a reciprocating manner such that pulsed flow is imparted to the liquid.

19. The device of claim 18 wherein the diaphragm has a circular configuration.

20. The device of claim 18 wherein the diaphragm has an annular configuration and substantially "C" shaped cross section.

21. The device of claim 19 wherein the oxygenator has an annular configuration and wherein the oxygenator, the pumping chamber, the diaphragm, the inlet duct, the delivery duct and the at least one lip valve are coaxial.

22. The device of claim 20 wherein the oxygenator has an annular configuration and wherein the oxygenator, the pumping chamber, the diaphragm, the inlet duct, the delivery duct and the at least one lip valve are coaxial.

23. The device of claim 17 further including a heat exchanger for controlling the temperature of blood, the heat exchanger being disposed within the body portion and having an inlet and an outlet through which blood flows along the blood flow route.

24. The device of claim 21 further including a heat exchanger for controlling the temperature of blood, the heat exchanger being disposed within the body portion and having an inlet and an outlet through which blood flows along the blood flow route.

25. The device of claim 22 further including a heat exchanger for controlling the temperature of blood, the heat exchanger being disposed within the body portion and having an inlet and an outlet through which blood flows along the blood flow route.

26. The device of claim 24 wherein the heat exchanger is of substantially cylindrical configuration and wherein the heat exchanger is coaxial with the oxygenator, the pumping chamber, the diaphragm, the inlet duct, the delivery duct and the at least one lip valve.

27. The device of claim 25 wherein the heat exchanger is of substantially cylindrical configuration and wherein the heat exchanger is coaxial with the oxygenator, the pumping chamber, the diaphragm, the inlet duct, the delivery duct and the at least one lip valve.

28. The device of claim 17 further including a venous reservoir disposed within the body portion, the venous reservoir having an inlet and an outlet through which blood flows along the blood flow route.

29. The device of claim 23 further including a venous reservoir disposed within the body portion, the venous reservoir having an inlet and an outlet through which blood flows along the blood flow route.

30. The device of claim 26 further including a venous reservoir disposed within the body portion, the venous reservoir being of substantially cylindrical configuration and having an inlet and an outlet through which blood flows along the blood flow route, the venous reservoir, the oxygenator, the heat exchanger, the pumping chamber, the diaphragm, the inlet duct, the delivery duct and the at least one lip valve being coaxial.

31. The device of claim 27 further including a venous reservoir disposed within the body portion, the venous reservoir being of substantially cylindrical configuration and having an inlet and an outlet through which blood flows along the blood flow route, the venous reservoir, the oxygenator, the heat exchanger, the pumping chamber, the diaphragm, the inlet duct, the delivery duct and the at least one lip valve being coaxial.

32. A device for the pulsed pumping of liquids, particularly blood, comprising:
a body portion;
a pumping chamber disposed within the body portion;
an inlet duct in fluid communication with the pumping chamber;
a delivery duct in fluid communication with the pumping chamber;
an inlet valve for controlling the flow of liquid from the inlet duct into the pumping chamber; and
a delivery valve for controlling the flow of liquid from the pumping chamber to the delivery duct, at least one of the inlet valve and the delivery valve being a lip valve which is movable between an open position and a closed position in dependence of fluid dynamic forces acting on the at least one lip valve and wherein at least one side of the at least one lip valve is fixed in the body portion.

33. The device of claim 32 wherein both the inlet valve and the delivery valve are lip valves.

34. The device of claim 32 further including a diaphragm disposed within the pumping chamber, the diaphragm being movable between a first position and a second position in a reciprocating manner such that pulsed flow is imparted to the liquid.

35. The device of claim 32 further including a fluid dynamic actuating device to impart fluid dynamic force to the liquid in the pumping chamber.

36. The device of claim 35 further including a diaphragm which is driven in a reciprocating manner by the actuating device between a first position and a second position such that pulsed flow is imparted to the liquid.

37. The device of claim 34 wherein the diaphragm has a circular configuration.

38. The device of claim 36 wherein the diaphragm has a circular configuration.

39. The device of claim 34 wherein the diaphragm has an annular configuration and a substantially "C" shaped cross section.

40. The device of claim 36 wherein the diaphragm has an annular configuration and a substantially "C" shaped cross section.

41. The device of claim 37 wherein the pumping chamber, the diaphragm, the inlet duct, the delivery duct, and the at least one lip valve are coaxial.

42. The device of claim 39 wherein the pumping chamber, the diaphragm, the inlet duct, the delivery duct, and the at least one lip valve are coaxial.

43. The device of claim 32 wherein the at least one lip valve comprises a first portion for anchoring the lip valve to the body portion and a second projecting portion which moves between the open position and the closed position.

44. The device of claim 33 wherein the lip valves comprise a first portion for anchoring the lip valve to the body portion and a second projecting portion which moves between the open position and the closed position.

45. The device of claim 32 further comprising a blood processing device selected from a venous reservoir, a heat exchanger, and an oxygenator, the blood processing device being disposed on a route along which the blood flows inside the body of the pumping device.

46. The device of claim 45 wherein the blood processing device, the pumping chamber, the diaphragm, the inlet duct, the delivery duct and the at least one lip valve are coaxial.

47. A cardiopulmonary bypass device comprising:
a body portion having a blood inlet and a blood outlet and between which is disposed a blood flow route;
a pump disposed within the body portion for the pulsed pumping of blood along the blood flow route, the pump including a pumping chamber, an inlet duct in fluid communication with the pumping chamber, a delivery duct in fluid communication with the pumping chamber, an inlet valve for controlling the flow of blood from the inlet duct into the pumping chamber, a delivery valve for controlling the flow of blood from the pumping chamber to the delivery duct, a diaphragm disposed within the pumping chamber, the diaphragm being movable between a first position and a second position in a reciprocating manner such that pulsed flow is imparted to the liquid and wherein the diaphragm has an annular configuration and is substantially "C" shaped in cross section, at least one of the inlet valve and the delivery valve being a lip valve having a projecting portion movable between an open position and a closed position in dependence of fluid dynamic forces acting on the at least one lip valve; and an oxygenator disposed within the body portion, the oxygenator having an inlet and an outlet through which blood flows along the blood flow route.

48. The device of claim 47 wherein the diaphragm has a circular configuration.

49. The device of claim 48 wherein the oxygenator has an annular configuration and wherein the oxygenator, the pumping chamber, the diaphragm, the inlet duct, the delivery duct and the at least one lip valve are coaxial.

50. The device of claim 47 wherein the oxygenator has an annular configuration and wherein the oxygenator, the pumping chamber, the diaphragm, the inlet duct, the delivery duct and the at least one lip valve are coaxial.

51. The device of claim 47 further including a heat exchanger for controlling the temperature of blood, the heat exchanger being disposed within the body portion and having an inlet and an outlet through which blood flows along the blood flow route.

52. The device of claim 49 further including a heat exchanger for controlling the temperature of blood, the heat exchanger being disposed within the body portion and having an inlet and an outlet through which blood flows along the blood flow route.

53. The device of claim 50 further including a heat exchanger for controlling the temperature of blood, the heat exchanger being disposed within the body portion and having an inlet and an outlet through which blood flows along the blood flow route.

54. The device of claim 52 wherein the heat exchanger is of substantially cylindrical configuration and wherein the heat exchanger is coaxial with the oxygenator, the pumping chamber, the diaphragm, the inlet duct, the delivery duct and the at least one lip valve.

55. The device of claim 53 wherein the heat exchanger is of substantially cylindrical configuration and wherein the heat exchanger is coaxial with the oxygenator, the pumping chamber, the diaphragm, the inlet duct, the delivery duct and the at least one lip valve.

56. The device of claim 47 further including a venous reservoir disposed within the body portion, the venous reservoir having an inlet and an outlet through which blood flows along the blood flow route.

57. The device of claim 47 further including a venous reservoir disposed within the body portion, the venous reservoir having an inlet and an outlet through which blood flows along the blood flow route.

58. The device of claim 54 further including a venous reservoir disposed within the body portion, the venous reservoir being of substantially cylindrical configuration and having an inlet and an outlet through which blood flows along the blood flow route, the venous reservoir, the oxygenator, the heat exchanger, the pumping chamber, the diaphragm, the inlet duct, the delivery duct and the at least one lip valve being coaxial.

59. The device of claim 55 further including a venous reservoir disposed within the body portion, the venous reservoir being of substantially cylindrical configuration and having an inlet and an outlet through which blood flows along the blood flow route, the venous reservoir, the oxygenator, the heat exchanger, the pumping chamber, the diaphragm, the inlet duct, the delivery duct and the at least one lip valve being coaxial.

* * * * *